United States Patent
Matsui et al.

(10) Patent No.: US 6,342,494 B1
(45) Date of Patent: Jan. 29, 2002

(54) CARBAPENEM COMPOUNDS, USE THEREOF, AND INTERMEDIATE COMPOUNDS OF THE SAME

(75) Inventors: Hiroshi Matsui, Nara; Masayasu Kasai, Yamatokoriyama, both of (JP)

(73) Assignee: Kyoto Pharmaceutical Industries, Ltd., Kyoto (JP)

( * ) Notice: Subject to any disclaimer, the term of this patent is extended or adjusted under 35 U.S.C. 154(b) by 0 days.

(21) Appl. No.: 09/355,757

(22) PCT Filed: Feb. 2, 1998

(86) PCT No.: PCT/JP98/00446

§ 371 Date: Aug. 4, 1999

§ 102(e) Date: Aug. 4, 1999

(87) PCT Pub. No.: WO98/34936

PCT Pub. Date: Aug. 13, 1998

(30) Foreign Application Priority Data

Feb. 7, 1997 (JP) .............................. 9-025671
Sep. 12, 1997 (JP) .............................. 9-248903

(51) Int. Cl.⁷ ................. C07D 477/20; A61K 31/407; A61P 31/04
(52) U.S. Cl. ................. 514/210.13; 540/350
(58) Field of Search ...................... 540/350; 514/210.13

(56) References Cited

U.S. PATENT DOCUMENTS

| | | | | |
|---|---|---|---|---|
| 4,740,507 A | * | 4/1988 | Sugimura | 540/350 |
| 4,888,344 A | * | 12/1989 | Sunagawa | 540/350 |
| 4,933,333 A | | 6/1990 | Sunagawa et al. | 514/192 |
| 5,523,415 A | | 6/1996 | Sendo et al. | 548/551 |
| 5,866,564 A | * | 2/1999 | Kawamoto | 540/350 |
| 6,090,802 A | | 7/2000 | Kawamoto et al. | 514/210 |

FOREIGN PATENT DOCUMENTS

| | | | |
|---|---|---|---|
| EP | 472062 | * | 2/1992 |
| JP | 1-34986 | | 2/1989 |
| JP | 01034986 | | 2/1998 |

OTHER PUBLICATIONS

Sunagawa, J. Antibiotics 49(11), Nov. 1996.*
Makoto Sunagawa et al., Synthesis and Biological Properties of 1 B–Methylcarbapenems with N–Methylpyrrolidinylthino Group at C–2 Position The Journal of Antibiotics, 1992, vol. 45, No. 6, pp. 971 and 976.
Makoto Sunagawa et al., Synthesis and Antibacterial Activity of Novel Carbapenems with a Catechol or Hydroxypyridrone Moiety The Journal of Antibiotics, 1994, vol. 47, No. 11, pp. 1354 and 1358.
Makoto Sunagawa et al., A Novel Carbapenem Antibiotic, SM–7338 Structure–Activity Relationships The Journal of Antibiotics, 1990, vol. 43, No. 5, pp. 519 and 532.
I. Kawamoto et al., Abstracts of the Interscience Conference on Antimicrobial Agents and Chemotherapy, vol. 36, No. 0, 1996, p 118.
T. Nishi et al., Abstracts of the Interscience Conference on Antimicrobial Agents and Chemotherapy, vol. 35, No. 0, 1995, p. 136.
U.S. Patent application Ser. No. 09/674,363, Filed Oct. 31, 2001, Matsui
The Journal of Antibiotics, vol. 45, pp. 971–976 (1992).
The Journal of Antibiotics, vol. 47, pp. 1354–1358 (1994).

* cited by examiner

*Primary Examiner*—Mark L. Berch
(74) *Attorney, Agent, or Firm*—Wenderoth, Lind & Ponack, L.L.P.

(57) ABSTRACT

A carbapenem compound of the formula (I)

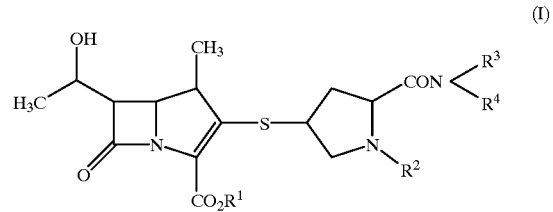

wherein $R^1$ is a group hydrolyzable in the body, $R^2$ is selected from the group consisting of aryl groups optionally substituted by 1–3 alkyl groups having 1–4 carbon atoms, 1-alkanoyloxyalkyl, 1-alkoxycarbonyloxyalkyl, phthalidyl and 5-methyl-2-oxo-1,3-dioxolen-4-ylmethyl, $R^3$ and $R^4$ are lower alkyl groups which may be the same or different or instead form a 4- to 6-membered cyclic amino with the adjacent nitrogen selected from the group consisting of azetidinyl, pyrrolidinyl and piperidinyl or a pharmaceutically acceptable salt thereof The carbapenem compound (I) and a pharmaceutically acceptable salt thereof of the present invention show superior absorption from digestive tract by oral administration, and sufficient antibacterial activity against a wide variety of bacterial species. Thus, they are extremely useful as agents for the prophylaxis and treatment of infectious diseases, particularly bacterial infectious diseases. Said agents for the prophylaxis and treatment of infectious diseases can be used as agents for the prophylaxis and treatment of the diseases caused by bacteria (e.g., suppurative diseases, respiratory infectious diseases, inflammatory diseases of biliary tract, urinary tract infection and the like) in warm-blooded animals inclusive of human (e.g., dog, cat, cow, horse, rat, mouse and the like).

11 Claims, No Drawings

1 …

CARBAPENEM COMPOUNDS, USE THEREOF, AND INTERMEDIATE COMPOUNDS OF THE SAME

TECHNICAL FIELD

The present invention relates to a novel carbapenem compound and a pharmaceutically acceptable salt thereof, which are useful as agents for the prophylaxis and treatment of bacterial infectious diseases. More particularly, the present invention relates to a novel carbapenem compound and a pharmaceutically acceptable salt thereof, which have sufficient antibacterial activity and which permit oral absorption; an oral antibacterial agent containing said compound as an active ingredient; and an intermediate compound for the production of said carbapenem compound and a salt thereof.

BACKGROUND ART

Many compounds having a carbapenem skeleton have been found as agents for treating infectious diseases, from which some carbapenem compounds having superior antibacterial activity have been put to practical use or under development for practical application. For example, a carbapenem compound of the formula (A)

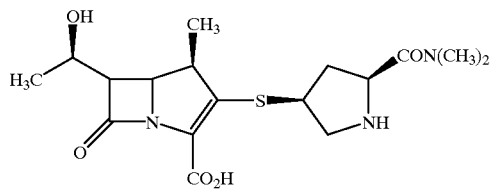

has been put to practical use and used in the clinical situations. This carbapenem compound has a broad antibacterial spectrum and potent antibacterial activity, and is free of instability to renal dehydropeptidase, which has been considered to be a drawback of conventional carbapenem compounds. It is a superior characteristic of this compound that it can be administered solely without using a stabilizer.

However, these carbapenem compounds show poor absorption from the digestive tract, which limits their clinical administration route to injection alone. An oral agent is easy and convenient to administer as compared to injections, and highly utilizable in clinical situations. Thus, there is a need for the development of a carbapenem compound for oral administration, which has potent antibacterial activity and broad antibacterial spectrum, and which shows superior absorption from the digestive tract.

It is therefore an object of the present invention to provide a carbapenem compound which has superior antibacterial activity and which shows superior absorption from the digestive tract.

Another object of the present invention is to provide use of said carbapenem compound.

A yet further object of the present invention is to provide an intermediate suitable for the production of said carbapenem compound.

DISCLOSURE OF THE INVENTION

The present inventors have conducted intensive studies in an attempt to achieve the above-mentioned objects, and found that a novel carbapenem compound of the following formula (I) and a pharmaceutically acceptable salt thereof show superior absorption from the digestive tract, have sufficiently potent antibacterial activity and are extremely useful as oral antibacterial agents. Further, the present inventors have found a novel intermediate compound usable for the production of said compound, which resulted in the completion of the present invention.

Accordingly, the present invention provides the following.

(1) A carbapenem compound (I) of the formula (I)

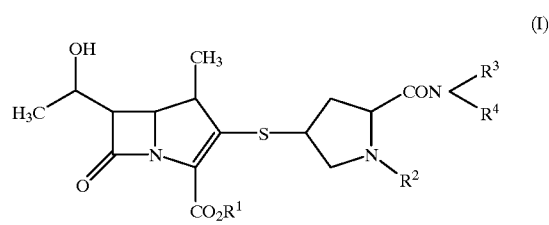

wherein
$R^1$ and $R^2$ may be the same or different and each is a modifying group hydrolyzable in the body;
$R^3$ and $R^4$ may be the same or different and each is a lower alkyl; or
$R^3$ and $R^4$ form a cyclic amino together with the adjacent nitrogen atom, and a pharmaceutically acceptable salt thereof.

(2) The carbapenem compound of (1) above, wherein $R^1$ and $R^2$ may be the same or different and each is a modifying group hydrolyzable in the body, and $R^3$ and $R^4$ may be the same or different and each is a lower alkyl, and a pharmaceutically acceptable salt thereof.

(3) The carbapenem compound of (1) above, wherein $R^2$ is 5-methyl-2-oxo-1,3-dioxolen-4-ylmethyl and $R^3$ and $R^4$ are each methyl, and a pharmaceutical acceptable salt thereof.

(4) The carbapenem compound of (1) above, wherein $R^1$ is pivaloyloxymethyl and $R^2$ is 5-methyl-2-oxo-1,3-dioxolen-4-ylmethyl, and a pharmaceutically acceptable salt thereof.

(5) The carbapenem compound of (1) above, wherein $R^1$ and $R^2$ are each pivaloyloxymethyl, and a pharmaceutically acceptable salt thereof.

(6) The carbapenem compound of (1) above, which is selected from the group consisting of
pivaloyloxymethyl (1R,5S,6S)-2-}(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate,
pivaloyloxymethyl (1R,5S,6S)-2-[(3S,5S)-(5-N,N-dimethylaminocarbonyl-1-pivaloyloxymethyl)pyrrolidin-3-ylthio]-6-[(1R)-1-hydroxyethyl]-1-methylcarbapen-2-em-3-carboxylate,
pivaloyloxymethyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate hydrochloride,
pivaloyloxymethyl (1R,5S,6S)-2-{(3S,5S)-[5-N,N-diethylaminocarbonyl-1-(5-methyl-2-oxo-1,3-dioxolen-4-yl)methyl]pyrrolidin-3-ylthio }-6-[(1R)-1-hydroxyethyl]-1-methylcarbapen-2-em-3-carboxylate,
pivaloyloxymethyl (1R,5S,6S)-2-{(3S,5S)-[5-N,N-methylethylaminocarbonyl-1-(5-methyl-2-oxo-1,3-dioxolen-4-yl)methyl]pyrrolidin-3-ylthio }-6-[(1R)-1-hydroxyethyl]-1-methylcarbapen-2-em-3-carboxylate, pivaloyloxymethyl (1R,5S,6S)-2-{(3S,5S)-[5-(1-pyrrolidinylcarbonyl)-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate, pivaloyloxymethyl (1R,5S,6S)-2-{(3S,5S)-[5-(1-piperidinylcarbonyl)-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate, and pivaloyloxymethyl (1R,5S,6S)-2-{(3S,5S)-[5-(1-azetidinylcarbonyl)-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate, and a pharmaceutically acceptable salt thereof.

(7) An antibacterial agent comprising the carbapenem compound of (1) above, which is represented by the formula (I) or a pharmaceutically acceptable salt thereof as an active ingredient.

(8) The antibacterial agent of (7) above, which is for oral administration.

(9) A carbapenem compound of the formula (II)

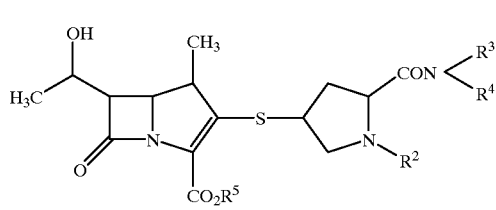

(II)

wherein
    $R^2$ is a modifying group hydrolyzable in the body;
    $R^3$ and $R^4$ may be the same or different and each is a lower alkyl; or
    $R^3$ and $R^4$ form a cyclic amino together with the adjacent nitrogen atom; and
    $R^5$ is a hydrogen atom or a carboxyl-protecting group, and a salt thereof.

(10) The carbapenem compound of (9) above, which is selected from the group consisting of
    p-nitrobenzyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate and
    sodium (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate,
and a salt thereof.

The modifying group hydrolyzable in the body at $R^1$ and $R^2$ is preferably hydrolyzed in intestine or blood, and is exemplified by optionally substituted aryl (e.g., phenyl, tolyl, xylyl, indanyl and the like), 1-alkanoyloxyalkyl, 1-alkoxycarbonyloxyalkyl, phthalidyl, 5-methyl-2-oxo-1,3-dioxolen-4-ylmethyl and the like. Particularly, 1-alkanoyloxyalkyl, 1-alkoxycarbonyloxyalkyl and 5-methyl-2-oxo-1,3-dioxolen-4-ylmethyl are preferable.

The optionally substituted aryl is preferably non-substituted or substituted by 1 to 3 substituents which may be the same or different. Examples of the substituent include alkyl having 1 to 4 carbon atoms such as methyl, ethyl and the like.

The number of the carbon atoms of the alkanoyl moiety of 1-alkanoyloxyalkyl is preferably 2 to 10, more preferably 2 to 7, and it may be linear, branched or cyclic. The number of the carbon atom of the alkyl moiety is preferably 1 to 3, more preferably 1 or 2.

Examples of 1-alkanoyloxyalkyl include acetoxymethyl, propionyloxymethyl, n-butyryloxymethyl, isobutyryloxymethyl, pivaloyloxymethyl, n-valeryloxymethyl, 2-methylbutyryloxymethyl, isovaleryloxymethyl, n-hexanoyloxymethyl, 3-methylvaleryloxymethyl, neohexanoyloxymethyl, 2-methylhexanoyloxymethyl, 2,2-dimethylvaleryloxymethyl, neoheptanoyloxymethyl, cyclohexanecarbonyloxymethyl, cyclohexylacetoxymethyl, 1-acetoxyethyl, 1-propionyloxyethyl, 1-n-butyryloxyethyl, 1-isobutyryloxyethyl, 1-n-valeryloxyethyl, 1-pivaloyloxyethyl, 1-isovaleryloxyethyl, 1-n-hexanoyloxyethyl, 1-cyclohexanecarbonyloxyethyl and the like.

The number of the carbon atom of the alkoxy moity of 1-alkoxycarbonyloxyalkyl is preferably 1 to 10, more preferably 1 to 7, and it may be linear, branched or cyclic. The number of the carbon atom of the alkyl moiety is preferably 1 to 3, more preferably 1 or 2.

The 1-alkoxycarbonyloxyalkyl is exemplified by 1-methoxycarbonyloxyethyl, 1-ethoxycarbonyloxyethyl, 1-n-propoxycarbonyloxyethyl, 1-isopropoxycarbonyloxyethyl, 1-n-butoxycarbonyloxyethyl, 1-secbutoxycarbonyloxyethyl, 1-t-butoxycarbonyloxyethyl, 1-pentyloxycarbonyloxyethyl and 1-cyclohexyloxycarbonyloxyethyl.

The lower alkyl at $R^3$ and $R^4$ is a linear or branched alkyl having 1 to 6 carbon atoms, which is exemplified by methyl, ethyl, propyl, isopropyl, butyl, isobutyl, sec-butyl, t-butyl, pentyl, isopentyl, neopentyl, t-pentyl, hexyl, isohexyl, neohexyl and the like. Particularly, methyl, ethyl, propyl and butyl are preferable.

The cyclic amino formed by $R^3$ and $R^4$ together with the adjacent nitrogen atom is a 4- to 6-membered cyclic amino. Examples of the above-mentioned cyclic amino include azetidinyl, pyrrolidinyl, piperidinyl and the like.

The carboxyl-protecting group at $R^5$ include, for example, t-butyl, t-amyl, benzyl, p-nitrobenzyl, p-methoxybenzyl, diphenylmethyl, p-nitrophenyl, methoxymethyl, ethoxymethyl, benzyloxymethyl, methylthiomethyl, trityl, 2,2,2-trichloroethyl, trimethylsilyl, diphenylmethoxybenzenesulfonylmethyl, dimethylaminoethyl and the like. Of these, p-nitrobenzyl, p-methoxybenzyl and diphenylmethyl are particularly preferable.

The carbapenem compound (I) and carbapenem compound (II) may form pharmaceutically acceptable salts.

Inasmuch as carbapenem compound (I) and carbapenem compound (II) have a basic group, they can form acid addition salts. The acid used for forming such acid addition salt is subject to no particular limitation as long as it is pharmaceutically acceptable. Examples of the acid include inorganic acids such as hydrochloric acid, sulfuric acid, phosphoric acid and nitric acid, organic acids such as oxalic acid, fumaric acid, maleic acid, citric acid, tartaric acid and methanesulfonic acid, and the like.

When carbapenem compound (II) has a carboxyl group (i.e., when $R^5$ is a hydrogen atom), a salt can be formed at said carboxyl group. Examples of the salt at carboxyl group include alkali metal salts (e.g., sodium salt, potassium salt and the like), alkaline earth metal salts (e.g., calcium salt, magnesium salt and the like), organic base salts (e.g., triethylamine salt, dicyclohexylamine salt, pyridine salt and the like), and the like.

The preferable examples of the carbapenem compound (I) and carbapenem compound (II) are the following:

pivaloyloxymethyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate, 1-pivaloyloxyethyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio }-6-[(1R)-1-hydroxyethyl]-1-methylcarbapen-2-em-3-carboxylate, 1-acetoxyethyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate, 1-isopropoxycarbonyloxyethyl (1R,5S,6S)-2-{(3S,5S)-[5-N,N-dimethylamino-carbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate, 1-ethoxycarbonyloxyethyl (1R,5S,6S)-2-{(3S,5S)-[5-N,N-dimethylamino-carbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate, 1-cyclohexyloxycarbonyloxyethyl (1R,5S,6S)-2-{(3S,5S)-[5-N,N-dimethyl-aminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate, (5-methyl-2-oxo-1,3-dioxolen-4-yl)methyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate, p-nitrobenzyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxy-ethyl]-1-methylcarbapen-2-em-3-carboxylate, diphenylmethyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate, p-methoxybenzyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate, (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylic acid, pivaloyloxymethyl (1R,5S,6S)-2-[(3S,5S)-(5-N,N-dimethylamninocarbonyl-1-pivaloyloxymethyl)pyrrolidin-3-ylthio]-6-[(1R)-1-hydroxyethyl]-1-methyl-carbapen-2-em-3-carboxylate, 1-pivaloyloxyethyl (1R,5S,6S)-2-[(3S,5S)-(5-N,N-dimethylaminocarbonyl-1-pivaloyloxymethyl)pyrrolidin-3-ylthio]-6-[(1R)-1-hydroxyethyl]-1-methyl-carbapen-2-em-3-carboxylate, 1-acetoxyethyl (1R,5S,6S)-2-[(3S,5S)-(5-N,N-dimethylarninocarbonyl-1-pivaloyloxymethyl)pyrrolidin-3-ylthio]-6-[(1R)-1-hydroxyethyl]-1-methyl-carbapen-2-em-3-carboxylate 1-isopropoxycarbonyloxyethyl (1R,5S,6S)-2-[(3S,5S)-(5-N,N-dimethylamino-carbonyl-1-pivaloyloxymethyl)pyrrolidin-3-ylthio]-6-[(1R)-1-hydroxyethyl]-1-methylcarbapen-2-em-3-carboxylate, 1-ethoxycarbonyloxyethyl (1R,5S,6S)-2-[(3S,5S)-(5-N,N-dimethylamino-carbonyl-1-pivaloyloxymethyl)pyrrolidin-3-ylthio]-6-[(1R)-1-hydroxyethyl]-1-methylcarbapen-2-em-3-carboxylate, 1-cyclohexyloxycarbonyloxyethyl (1R,5S,6S)-2-[(3S,5S)-(5-N,N-dimethylaminocarbonyl-1-pivaloyloxymethyl)pyrrolidin-3-ylthio]-6-[(1R)-1-hydroxyethyl]-1-methylcarbapen-2-em-3-carboxylate, (5-methyl-2-oxo-1,3-dioxolen-4-yl)methyl-(1R,5S,6S)-2-[(3S,5S)-(5-N,N-dimethylaminocarbonyl-1-pivaloyloxymethyl)pyrrolidin-3-ylthio]-6-[(1R)-1-hydroxyethyl]-1-methylcarbapen-2-em-3-carboxylate, p-nitrobenzyl (1R,5S,6S)-2-[(3S,5S)-(5-N,N-dimethylarninocarbonyl-1-pivaloyloxymethyl)pyrrolidin-3-ylthio]-6-[(1R)-1-hydroxyethyl]-1-methyl-carbapen-2-em-3-carboxylate, diphenylmethyl (1R,5S,6S)-2-[(3S,5S)-(5-N,N-dimethylaminocarbonyl-1-pivaloyloxymethyl)pyrrolidin-3-ylthio]-6-[(1R)-1-hydroxyethyl]-1-methyl-carbapen-2-em-3-carboxylate, p-methoxybenzyl (1R,5S,6S)-2-[(3S,5S)-(5-N,N-dimethylaminocarbonyl-1-pivaloyloxymethyl)pyrrolidin-3-ylthio]-6-[(1R)-1-hydroxyethyl]-1-1-methyl-carbapen-2-em-3-carboxylate, (1R,5S,6S)-2-[(3S,5S)-(5-N,N-dimethylaminocarbonyl-1-pivaloyloxymethyl)-pyrrolidin-3-ylthio]-6-[(1R)-1-hydroxyethyl]-1-methylcarbapen-2-em-3-carboxylic acid, pivaloyloxymethyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate hydrochloride, pivaloyloxymethyl (1R,5S,6S)-2-{(3S,5S)-[5-N,N-diethylaminocarbonyl-1-(5-methyl-2-oxo-1,3-dioxolen-4-yl)methyl]pyrrolidin-3-ylthio}-6-[(1R)-1-hydroxy-ethyl]-1-methylcarbapen-2-em-3-carboxylate, pivaloyloxymethyl (1R,5S,6S)-2-{(3S,5S)-[5-N,N-methylethylaminocarbonyl-1-(5-methy-2-oxo-1,3-dioxolen-4-yl)methyl]pyrrolidin-3-ylthio}-6-[(1R)-1-hydroxyethyl]-1-methylcarbapen-2-em-3-carboxylate, pivaloyloxymethyl (1R,5S,6S)-2-{(3S,5S)-[5-(1-pyrrolidinylcarbonyl)-1-(5-methyl-2-oxo-1,3-dioxolen-4-yl)methyl]pyrrolidin-3-ylthio }-6-[(1R)-1-hydroxyethyl]-1-methylcarbapen-2-em-3-carboxylate, pivaloyloxymethyl (1R,5S,6S)-2-{(3S,5S)-[5-(1-piperidinylcarbonyl)-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate, and pivaloyloxymethyl (1R,5S,6S)-2-{(3S,5S)-[5-(1-azetidinylcarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate, and the like.

The carbapenem compound (I) and a pharmaceutically acceptable salt thereof, and carbapenem compound (II) and a pharmaceutically acceptable salt thereof can be produced by any of the following production methods 1 to 4.

Production Method 1

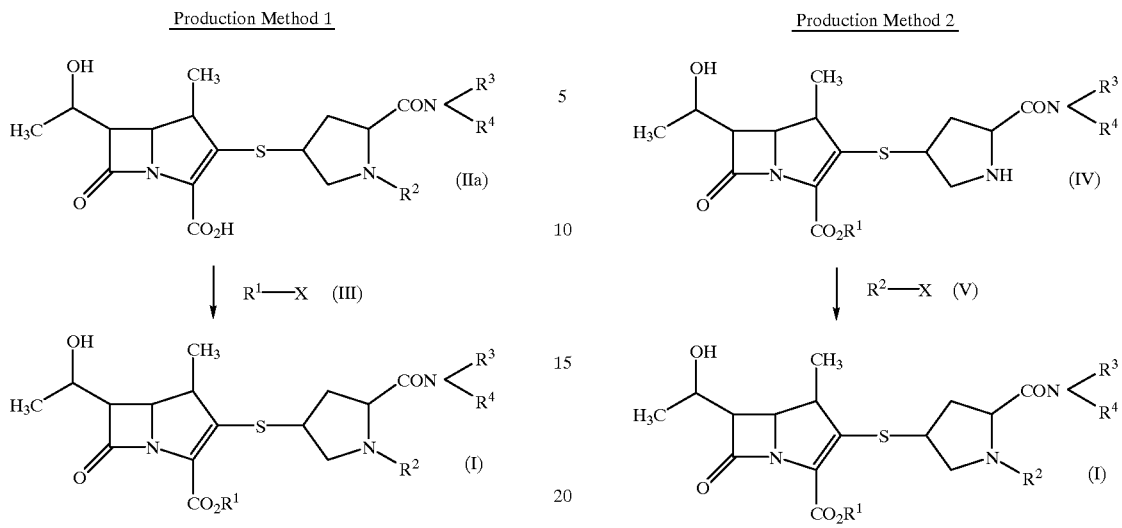

wherein R¹, R², R³ and R⁴ are as defined above, and X is a leaving group such as a halogen atom (e.g., chlorine, bromine and iodine), alkanesulfonyloxy (e.g., methanesulfonyloxy, ethanesulfonyloxy, propanesulfonyloxy and butanesulfonyloxy), arylsulfonyloxy (e.g., phenylsulfonyloxy and tolylsulfonyloxy), and the like.

Compound (I) can be obtained by dissolving compound (IIa) (compound of formula (II) wherein $R^5$ is hydrogen atom) in a solvent which does not interfere with the reaction (e.g., dioxane, acetonitrile, tetrahydrofuran, chloroform, methylene chloride, ethylene chloride, benzene, ethyl acetate, N,N-dimethylformamide, N,N-dimethylacetamide, dimethyl sulfoxide and mixtures thereof), and reacting the compound with about 1–5 times, preferably about 1–2 times, the molar amount of compound (III) in the presence of a base.

The base to be used is subject to no particular limitation, but it is preferably an inorganic base such as sodium hydrogencarbonate, potassium carbonate and the like, an organic base such as triethylamine and diisopropylethylamine, and the like.

The reaction temperature is not particularly limited, but the reaction is preferably carried out at a relatively low temperature to suppress side reaction, which is generally −30–40° C., preferably −20–0°C. While the reaction time varies depending mainly on reaction temperature, the kind of reaction reagents and the like, it is generally from 30 minutes to a dozen hours or so.

Where necessary, compound (IIa) can be introduced into a reactive derivative thereof such as alkali metal salt (e.g., sodium salt, potassium salt and the like), alkaline earth metal salt (e.g., calcium salt), triethylamine salt, dicyclohexylamine salt, pyridine salt, and the like, and reacted with compound (III).

Production Method 2 wherein R¹, R², R³, R⁴ and X are as defined above.

Compound (I) can be obtained by dissolving compound (IV) in a solvent which does not interfere with the reaction (e.g., dioxane, acetonitrile, tetrahydrofuran, chloroform, methylene chloride, ethylene chloride, benzene, ethyl acetate, N,N-dimethylformamide, N,N-dimethylacetamide, dimethyl sulfoxide and mixtures thereof), and reacting the compound with about 1 5 times, preferably about 1 2 times, the molar amount of compound (V). Compound (IV) can be obtained by reacting the carboxylic acid disclosed in Japanese Pat. Unexamined Publication No. 233076/1985 and the like, and compound (III), in the same manner as in Production Method 1.

This reaction can be also carried out in the presence of a base. The base to be used is subject to no particular limitation, but it is preferably an inorganic base, such as sodium hydrogencarbonate, potassium carbonate and the like, or an organic base, such as triethylamine, diisopropylethylamine and the like.

The reaction temperature is not particularly limited, but the reaction is preferably carried out at a relatively low temperature to suppress side reaction, which is generally −30–40° C., preferably −20–0° C. While the reaction time varies depending mainly on reaction temperature, the kind of reaction reagents and the like, it is generally from 30 minutes to a dozen hours or so.

Production Method 3

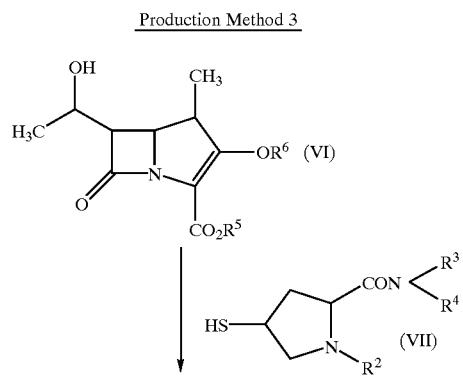

-continued

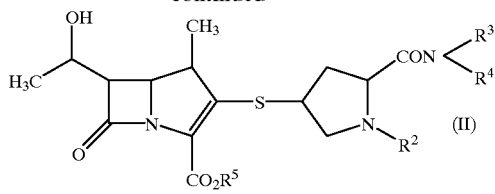
(II)

wherein $R^2$, $R^3$, $R^4$ and $R^5$ are as defined above and $R^6$ is alkanesulfonyl, such as methanesulfonyl, ethanesulfonyl, propanesulfonyl, butanesulfonyl and the like, arylsulfonyl, such as phenylsulfonyl, tolylsulfonyl and the like, dialkylphosphoryl, such as dimethylphosphoryl, diethylphosphoryl, diisopropylphosphoryl, dibutylphosphoryl and the like, or diarylphosphoryl, such as diphenylphosphoryl, ditolylphosphoryl and the like.

Compound (II) can be obtained by dissolving compound (VI) disclosed in Japanese Patent Unexamined Publication No. 12676/1996 and the like in a solvent which does not interfere with the reaction (e.g., dioxane, acetonitrile, tetrahydrofuran, chloroform, methylene chloride, ethylene chloride, benzene, ethyl acetate, N,N-dimethylformamide, N,N-dimethylacetamide, dimethyl sulfoxide and mixtures thereof), and reacting the compound with about 1–5 times, preferably about 1–3 times, the molar amount of mercapto compound (VII) in the presence of a base.

The base to be used is subject to no particular limitation, but it is preferably an inorganic base, such as sodium hydrogencarbonate, potassium carbonate and the like, or an organic base, such as triethylamine, diisopropylethylamine and the like.

The reaction temperature is not particularly limited, but the reaction is preferably carried out at a relatively low temperature to suppress side reaction, which is generally −30–40° C., preferably −20–0° C. While the reaction time varies depending mainly on reaction temperature, the kind of reaction reagents and the like, it is generally from 30 minutes to a dozen hours or so.

The starting compound (VII) for the synthesis of compound (II) can be obtained in the following manner.

Production Method of compound (VII)

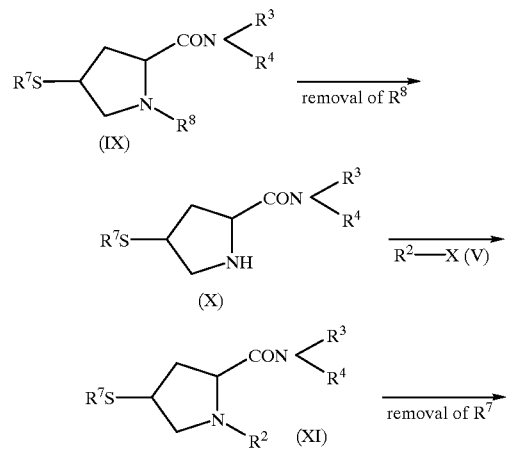

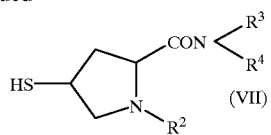
(VII)

wherein $R^2$, $R^3$, $R^4$ and X are as defined above, $R^7$ is a thiol-protecting group and $R^8$ is an amino-protecting group.

Compound (VII) can be obtained by removing $R^8$, which is an amino-protecting group of compound (IX) disclosed in Japanese Patent Unexamined Publication No. 233076/1985 and the like, by a method known per se to give compound (X), reacting compound (X) and compound (V) in the same manner as in Production Method 2 to give compound (XI), and removing $R^7$, which is a thiol-protecting group by a method known per se. As the thiol- and amino-protecting groups, the protecting groups generally known in the pertinent field can be used.

Production Method 4

[Structure (VIII)]

↓ $R^2$—X (V)

[Structure (II)]

Wherein $R^2$, $R^3$·$R^4$ $R^5$ and X are as defined above.

Compound (II) can be obtained by reacting compound (VIII) disclosed in Japanese Patent Unexamined Publication No. 233076/1985 and the like, and compound (V) in the same manner as in Production Method 2.

Where necessary, the carbapenem compound (II) thus obtained can be converted to a carboxylic acid derivative wherein $R^5$ is hydrogen atom by removing carboxyl-protecting group, according to a conventional method. While the method for the removal of a protecting group varies depending on the kind thereof, a method generally known in this field can be used.

The carbapenem compound (I) and carbapenem compound (II) can be purified as necessary according to a conventional method, such as recrystallization, preparative thin layer chromatography, column chromatography and the like. Alternatively, it can be purified as salts thereof, where necessary.

The carbapenem compound (I) and carbapenem compound (II) can be converted to a pharmaceutically acceptable salt thereof by a method known per se.

The objective compound (I) and compound (II) of the present invention preferably have a configuration of compound (Ia) and compound (IIb) below.

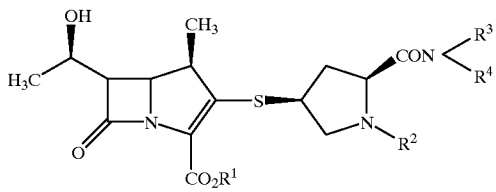

(Ia)

wherein $R^1$, $R^2$, $R^3$ and $R^4$ are as defined above.

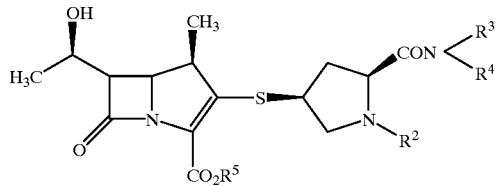

(IIb)

wherein $R^2$, $R^3$, $R^4$ and $R^5$ are as defined above.

The carbapenem compound (I) and a pharmaceutically acceptable salt thereof are promptly absorbed in blood by oral administration, and metabolized into a carbapenem compound of the formula (I) wherein $R^1$ and $R^2$ are hydrogen atom, or a pharmaceutically acceptable salt thereof, and show high concentration in blood.

In addition, carbapenem compound (I) upon conversion into a pharmaceutically acceptable salt thereof shows enhanced solubility in the digestive tract, which in turn further improves absorption effect, and thus, absorption property.

Therefore, an agent for the prophylaxis and treatment of infectious diseases comprising carbapenem compound (I) or a pharmaceutically acceptable salt thereof shows superior action by oral administration as mentioned above, and can be generally administered as an oral preparation.

This agent for the prophylaxis and treatment of infectious diseases can be produced by diluting the compound with pharmaceutical excipients by a method known per se. Examples of usable excipient include starch, lactose, sugar, calcium carbonate, calcium phosphate and the like.

Moreover, this agent for the prophylaxis and treatment of infectious diseases preferably contains an organic acid, whereby carbapenem compound (I) and a pharmaceutically acceptable salt thereof are caused to have higher solubility in the digestive tract, thus facilitating absorption thereof into blood.

The organic acid may be any as long as it is pharmaceutically acceptable, and is preferably exemplified by organic carboxylic acids such as maleic acid, fumaric acid, tartaric acid, citric acid, succinic acid, malic acid, oxalic acid, mandelic acid, malonic acid, benzoic acid and the like. The organic acid is generally added in an amount of 0.01–20 moles, preferably 0.02–2 moles, per mole of carbapenem compound (I) or a pharmaceutically acceptable salt thereof.

Further, this agent for the prophylaxis and treatment of infectious diseases may contain other additives on demand, such as binders (e.g., starch, gum arabic, carboxymethylcellulose, hydroxypropylcellulose, crystalline cellulose and the like), lubricants (e.g., magnesium stearate, talc and the like), disintegrators (e.g., carboxymethylcellulose calcium, talc and the like), and the like. After adding various ingredients, the obtained mixture is formulated into a dosage form suitable for oral administration, such as capsules, tablets, fine granules, granules, dry syrups and the like, by a method known per se to give an agent for oral administration, which is for the prophylaxis and treatment of infectious diseases.

While the dose of carbapenem compound (I) and a pharmaceutically acceptable salt thereof varies depending on the administration target, symptom, and others, when, for example, the compound is administered to treat suppurative diseases of an adult, the daily dose is about 1–40 mg/kg body weight, which is orally administered 1 to 4 times a day.

Said carbapenem compound (I) and a pharmaceutically acceptable salt thereof may be administered in combination with other antibacterial substance, such as antibacterial drugs (e.g., penicillins, aminoglycosides, cephalosporins and the like) or a therapeutic agent for systemic symptoms caused by bacterial infection (e.g., antipyretic, analgesic, antiinflammatory drug and the like).

The properties and production methods of the compounds of the present invention are explained by way of Examples, to which the present invention is not limited.

EXAMPLE 1 p-Nitrobenzyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate (2S,4S)-2-N,N-Dimethylaminocarbonyl-4-mercapto-1-(5-methyl-2-oxo-1,3-dioxolen-4-yl)methylpyrrolidine (867 mg) was dissolved in acetonitrile (11 ml), and a solution of p-nitrobenzyl (1R,5S,6S)-2-diphenylphosphoro-6-[(1R)-1-hydroxyethyl]-1-methylcarbapen-2-em-3-carboxylate (1.5 g) and diisopropylethylamine (1.05 ml) in acetonitrile (15 ml) was dropwise added under nitrogen atmosphere at −40−−30° C. The mixture was stirred at the same temperature for one hour, and ethyl acetate (200 ml) was added. The reaction mixture was washed with saturated brine (100 ml) and dried over anhydrous sodium sulfate. Ethyl acetate was evaporated under reduced pressure and the residue was purified by silica gel column chromatography to give 1.0 g of the title compound.

$^1$H-NMR(DMSO-$d_6$) δ ppm: 1.06(d, J=7.5 Hz, 3H), 1.16 (d, J=6.5 Hz, 3H), 1.30~1.80(m, 1H), 2.02(s, 3H), 2.50~4.30 (m, 9H), 2.82(s, 3H), 3.01 (s, 3H), 3.57(s, 2H), 5.01 (d, J=5.0 Hz, 1H), 5.25, 5.50(ABq, J=13.5 Hz, 2H), 7.67, 8.22(ABq, J=8.5 Hz, 4H).

EXAMPLE 2

Sodium (1R,5S,6)-2-{(3S,5S)-[5-N,N-dimethylaminocarbonyl-1(5-methyl-2-oxo-1,3-dioxolen-4-yl)methyl]pyrrolidin-3-ylthio}-6-[(1R)-1-hydroxyethyl]-1-methylcarbapen-2-em-3-carboxylate.

p-Nitrobenzyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate (730 mg) was dissolved in a mixed solution of tetrahydrofuran (22 ml) and 0.1 M phosphate buffer (pH 7.0, 33 ml), and 10% palladium carbon (550 mg) was added. The mixture was hydrogenated at room temperature for 2.5 hours. The reaction mixture was filtered through Celite and the filtrate obtained was washed with diethyl ether and concentrated under reduced pressure to about 5 ml. The obtained solution was subjected to chromatography on Dia Ion HP-21 (manufactured by Mitsubishi Chemical). After concentration under reduced pressure, the residue was lyophilized to give 300 mg of the title compound.

IR(Nujol, cm$^{-1}$):3385, 1815, 1750, 1600. $^1$H-NMR (DMSO-d$_6$) δ ppm: 1.05(d, J=7.5 Hz, 3H), 1.15(d, J=6.5 Hz, 3H), 1.20~1.70(m, 1H), 2.03(s, 3H), 2.50~4.20(m, 9H), 2.81(s, 3H), 3.01 (s, 3H), 3.60(s, 2H), 4.40~5.50(br, 1H).

EXAMPLE 3

Pivaloyloxymethyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate.

Sodium (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbarbapen-2-em-3-carboxylate (500 mg) was dissolved in N,N-dimethylformamide (2.5 ml) and the mixture was cooled to −5° C. Pivaloyloxymethyl iodide (350 mg) was added, and the mixture was stirred at the same temperature for one hour. Ethyl acetate (100 ml) was added and the reaction mixture was washed with 5% brine (100 ml) and dried over anhydrous sodium sulfate. Ethyl acetate was evaporated under reduced pressure and the residue was purified by silica gel column chromatography to give 370 mg of the title compound.

IR(Nujol, cm$^{-1}$):3400, 1820, 1755, 1640. $^1$H-NMR (DMSO-d$_6$) δ ppm: 1.00~1.30(m, 15H), 1.30~1.80(m, 1H), 2.03(s, 3H), 2.50~4.30(m, 9H), 2.82(s, 3H), 3.01 (s, 3H), 3.55(s, 2H), 5.00(d, J=5.0 Hz, 1H), 5.70, 5.87(ABq, J=5.5 Hz, 2H).

EXAMPLE 4

Pivaloyloxymethyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate (1) Sodium (1R,5S,6S)-2-[(3S,5S)-5-N,N-dimethylaminocarbonylpyrrolidin-4-ylthio]-6-[(1R)-1-hydroxyethyl]-1-methylcarbapen-2-em-3-carboxylate (580 mg) was suspended in N,N-dimethylformamide (2.9 ml) and the mixture was cooled to −5° C. Pivaloyloxymethyl iodide (520 mg) was added, and the mixture was stirred at the same temperature for one hour. Ethyl acetate (150 ml) was added and the mixture was washed with 5% brine (150 ml) and dried over anhydrous sodium sulfate. Ethyl acetate was evaporated under reduced pressure and the residue was purified by silica gel column chromatography to give 350 mg of pivaloyloxymethyl (1R,5S,6S)-2-[(3S,5S)-5-N,N-dimethyl-aminocarbonylpyrrolidin-4-ylthio]-6-[(1R)-1-hydroxyethyl]-1-methylcarbapen-2-em-3-carboxylate.

$^1$H-NMR(DMSO-d$_6$) δ ppm: 1.02~1.30(m, 15H), 1.30~1.80(m, 1 H), 2.50~4.40(m, 10H), 2.87(s, 3H), 2.99(s, 3H), 4.90~5.10(m, 1H), 5.70, 5.85(ABq, J=6.0 Hz, 2H).

(2) The compound (330 mg) obtained in Example 4 (1) was dissolved in N,N-dimethylformamide (1.7 ml) and the mixture was cooled to 5° C. (5-Methyl-2-oxo-1,3-dioxolen-4-yl)methyl bromide (190 mg) and triethylamine (0.11 ml) were added, and the mixture was stirred at the same temperature for 1.5 hours. Ethyl acetate (150 ml) was added and the mixture was washed with 5% brine (100 ml) and aqueous layer was extracted twice with ethyl acetate (150 ml). The ethyl acetate layers were combined and dried over anhydrous sodium sulfate. Ethyl acetate was evaporated under reduced pressure and the residue was purified by silica gel column chromatography to give 230 mg of the title compound.

IR and $^1$H-NMR matched with those in Example 3.

EXAMPLE 5

Pivaloyloxymethyl (1R,5S,6S)-2-[(3S,5S)-(5-N,N-dimethylaminocarbonyl-1-pivaloyloxymethyl)pyrrolidin-3-ylthio]-6-[(1R)-1-hydroxyethyl]-1-methylcarbapen-2-em-3-carboxylate.

Pivaloyloxymethyl (1R,5S,6S)-2-[(3S,5S)-5-N,N-dimethylaminocarbonyl-pyrrolidin-4-ylthio]-6-[(1R)-1-hydroxyethyl]-1-methylcarbapen-2-em-3-carboxylate (400 mg) obtained in Example 4 (1) and pivaloyloxymethyl iodide (290 mg) were reacted in the same manner as in Example 4 (2) to give 190 mg of the title compound.

$^1$H-NMR(DMSO-d$_6$) δ ppm: 1.02~1.30(m, 24H), 1.30~1.80(m, 1H), 2.50~4.40(m, 10H), 2.87(s, 3H), 2.99(s, 3H), 4.90~5.10(m, 1H), 5.70, 5.85(ABq, J=6.0 Hz, 2H).

EXAMPLE 6

Pivaloyloxymethyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate hydrochloride Pivaloyloxymethyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate (1.49 g) obtained in Example 3 was dissolved in ethyl acetate (30 ml) and the mixture was cooled to 5° C. A solution (0.35 ml) of hydrogen chloride dissolved in 2-propanol at 8.68N was added, and the mixture was stirred at the same temperature for 15 minutes. The resulting crystals were collected by filtration and washed with ethyl acetate and then with diethyl ether to give 1.2 g of the title compound.

IR(Nujol, cm$^{-1}$):3355, 1825, 1770, 1740, 1660. $^1$H-NMR (D$_2$O) δ ppm: 1.10~1.40(m, 6H), 1.19(s, 9H), 1.70~2.10(m, 1H), 2.19(s, 3H), 2.80~3.20(m, 1H), 2.99(s, 3H), 3.09(s, 3H), 3.30~3.70(m, 2H), 3.80~4.10(m, 2H), 4.10~4.50(m, 5H), 4.80–5.00 (m, 1H), 5.86, 5.96(ABq, J=6.0 Hz, 2H).

The compounds of Examples 7 to 11 were synthesized in the same manner as in any one of Examples 1 to 5 and their properties were determined.

EXAMPLE 7

Pivaloyloxymethyl (1R,5S,6S)-2-{(3S,5S)-[5-N,N-diethylamninocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate $^1$H-NMR(DMSO-d$_6$) δ ppm: 1.10~1.30(m, 21H), 1.30~1.80(m, 1H), 2.03(s, 3H), 2.50~4.30(m, 13H), 3.56(s, 2H), 5.10(d, J=5.0 Hz, 1H), 5.66, 5.85(ABq, J=5.5 Hz, 2H).

EXAMPLE 8

Pivaloyloxymethyl (1R,5S,6S)-2-{(3S,5S)-[5-N,N-methylethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate $^1$H-NMR(DMSO-d$_6$) δ ppm: 1.10~1.30(m, 18H), 1.30~1.80(m, 1H), 2.05(s, 3H), 2.50~4.30(m, 11H), 2.93, 3.03(s, s, 3H), 3.58(s, 2H), 5.05(d, J=5.0 Hz, 1H), 5.68, 5.87(ABq, J=5.5 Hz, 2H).

EXAMPLE 9

Pivaloyloxymethyl (1R,5S,6S)-2-{(3S,5S)-[5-(1-pyrrolidinylcarbonyl)-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate $^1$H-NMR(DMSO-d$_6$) δ ppm: 1.00~1.30(m, 15H), 1.30~1.80(m, 1H), 1.80~2.10(m, 4H), 2.05(s, 3H), 2.50~4.30(m, 13H), 3.58(s, 2H), 5.07(d, J=5.0 Hz, 1H), 5.67, 5.83(ABq, J=5.5 Hz, 2H).

EXAMPLE 10

Pivaloyloxymethyl (1R,5S,6S)-2-{(3S,5S)-[5-(1-piperidinylcarbonyl)-1-(5-methyl-2-oxo1,3-dioxolen-4-yl)

methyl]pyrrolidin-3-ylthio}-6-[(iR)-1-hydroxyethyl]-1-methylcarbapen-2-em-3-carboxylate.

$^1$H-NMR(DMSO-d$_6$) δ ppm: 1.00~1.30(m, 15H), 1.30~1.80(m, 7H), 2.03(s, 3H), 2.50~4.30(m, 13H), 3.57(s, 2H), 5.10(d, J=5.0 Hz, 1H), 5.66, 5.83(ABq, J=5.5 Hz, 2H).

EXAMPLE 11

Pivaloyloxymethyl (1R,5S,6S)-2-{(3S,5S)-[5-(1-azetidinylcarbonyl)-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate.

$^1$H-NMR(DMSO-d$_6$) δ ppm: 1.00~1.30(m, 15H), 1.30~1.80(m, 1H), 2.05(s, 3H), 2.50~4.50(m, 15H), 3.57(s, 2H), 5.05(d, J=5.0 Hz, 1H), 5.68, 5.85(ABq, J=5.5 Hz, 2H).

The following compounds were obtained by the method described in any of the abovementioned Examples 1 to 5.

(1) 1-pivaloyloxyethyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate (2) 1-acetoxyethyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate (3) 1-isopropoxycarbonyloxyethyl (1R,5S,6S)-2-{(3S,5S)-[5-N,N-dimethyl-aminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate (4) 1-ethoxycarbonyloxyethyl (1R,5S,6S)-2-{(3S,5S)-[5-N,N-dimethyl-aminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate (5) 1-cyclohexyloxycarbonyloxyethyl (1R,5S,6S)-2-{(3S,5S)-[5-N,N-dimethyl-aminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate (6) (5-methyl-2-oxo-1,3-dioxolen-4-yl)methyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate (7) diphenylmethyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate (8) p-methoxybenzyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio }-6-[(1R)-1-hydroxyethyl]-1-methylcarbapen-2-em-3-carboxylate (9) 1-pivaloyloxyethyl (1R,5S,6S)-2-[(3S,5S)-(5-N,N-dimethylaminocarbonyl-1-pivaloyloxymethyl)pyrrolidin-3-ylthio]-6-[(1R)-1-hydroxyethyl]-1-methylcarbapen-2-em-3-carboxylate

(10) 1-acetoxyethyl (1R,5S,6S)-2-[(3S,5S)-(5-N,N-dimethylamninocarbonyl-1-pivaloyloxymethyl)pyrrolidin-3-ylthio]-6-[(1R)-1-hydroxyethyl]-1-methylcarbapen-2-em-3-carboxylate

(11) 1-isopropoxycarbonyloxyethyl (1R,5S,6S)-2-[(3S,5S)-(5-N,N-dimethyl-aminocarbonyl-1-pivaloyloxymethyl)pyrrolidin-3-ylthio]-6-[(1R)-1-hydroxyethyl]-1-methylcarbapen-2-em-3-carboxylate

(12) 1-ethoxycarbonyloxyethyl (1R,5S,6S)-2-[(3S,5S)-(5-N,N-dimethylamino-carbonyl-1-pivaloyloxymethyl)pyrrolidin-3-ylthio]-6-[(1R)-1-hydroxyethyl]-1-methylcarbapen-2-em-3-carboxylate

(13) 1-cyclohexyloxycarbonyloxyethyl (1R,5S,6S)-2-[(3S,5S)-(5-N,N-dimethyl-aminocarbonyl-1-pivaloyloxymethyl)pyrrolidin-3-ylthio]-6-[(1R)-1-hydroxyethyl]-l1-methylcarbapen-2-em-3-carboxylate

(14) (5-methyl-2-oxo-1,3-dioxolen-4-yl)methyl (1R,5S,6S)-2-[(3S,5S)-(5-N,N-dimethylaminocarbonyl-1-pivaloyloxymethyl)pyrrolidin-3-ylthio]-6-[(1R)-1-hydroxyethyl]-1-methylcarbapen-2-em-3-carboxylate

(15) p-nitrobenzyl (1R,5S,6S)-2-[(3S,5S)-(5-N,N-dimethylaminocarbonyl-1-pivaloyloxymethyl)pyrrolidin-3-ylthio]-6-[(1R)-1-hydroxyethyl]-1-methylcarbapen-2-em-3-carboxylate

(16) diphenylmethyl (1R,5S,6S)-2-[(3S,5S)-(5-N,N-dimethylaminocarbonyl-1-pivaloyloxymethyl)pyrrolidin-3-ylthio]-6-[(1R)-1-hydroxyethyl]-1-methylcarbapen-2-em-3-carboxylate

(17) p-methoxybenzyl (1R,5S,6S)-2-[(3S,5S)-(5-N,N-dimethylaminocarbonyl-1-pivaloyloxymethyl)pyrrolidin-3-ylthio]-6-[(1R)-1-hydroxyethyl]-1-methylcarbapen-2-em-3-carboxylate

(18) (1R,5S,6S)-2-[(3S,5S)-(5-N,N-dimethylaminocarbonyl-1-pivaloyl-oxymethyl)pyrrolidin-3-ylthio]-6-[(1R)-1-hydroxyethyl]-1-methylcarbapen-2-em-3-carboxylate.

Then, the following oral absorption tests were conducted to clarify the superior property of the compound of the present invention.

EXPERIMENTAL EXAMPLE 1 (oral absorption test)

The compound of the present invention (compound of Example 6, 20 mg/kg) was orally administered to dogs (3 per group) and urinary hydrolyzed carbapenem compound (A) concentration at 0–3, 3–6 and 6–24 hours later was measured by a paper disc method using test bacteria *Escherichia coli* NIHJ and nutrient agar medium (Difco). The urinary recovery percentage was determined. The results are shown in Table 1.

TABLE 1

| Test compound | urinary recovery (%) | | | |
| --- | --- | --- | --- | --- |
| | 0–3 hr | 3–6 hr | 6–24 hr | 0–24 hr |
| Example 6 | 10.3 | 2.4 | 0.3 | 13.0 |

EXPERIMENTAL EXAMPLE 2 (oral absorption test)

The compound of the present invention (compound of Example 6, 20 mglkg) was orally administered to dogs (3 per group) and plasma hydrolyzed carbapenem compound (A) concentration at 0.25, 0.5, 1.0, 1.5, 2.0, 3.0, 4.0 and 6.0 hours later was measured by a paper disc method using test bacteria *Escherichia coli* NIHJ and nutrient agar medium (Difco). The results are shown in Table 2 and Table 3.

| Test | concentration in plasma (μg/ml) | | | |
|---|---|---|---|---|
| compound | 0.25 hr | 0.5 hr | 1.0 hr | 1.5 hr |
| Example 6 | 5.06 | 6.56 | 7.60 | 7.67 |

TABLE 3

| Test | concentration in plasma (μg/ml) | | | |
|---|---|---|---|---|
| compound | 2.0 hr | 3.0 hr | 4.0 hr | 6.0 hr |
| Example 6 | 5.92 | 3.68 | 1.92 | 0.43 |

The carbapenem compound (I) and a pharmaceutically acceptable salt thereof of the present invention show superior absorption from digestive tract by oral administration, and sufficient antibacterial activity against a wide variety of bacterial species. Thus, they are extremely useful as agents for the prophylaxis and treatment of infectious diseases, particularly bacterial infectious diseases. Said agents for the prophylaxis and treatment of infectious diseases can be used as agents for the prophylaxis and treatment of the diseases caused by bacteria (e.g., suppurative diseases, respiratory infectious diseases, inflammatory diseases of biliary tract, urinary tract infection and the like) in warm-blooded animals inclusive of human (e.g., dog, cat, cow, horse, rat, mouse and the like).

This invention is based on application Nos. 25671/1997 and 248903/1997 filed in Japan, the contents of which are incorporated hereinto by reference.

What is claimed is:

1. A carbapenem compound of the formula (I):

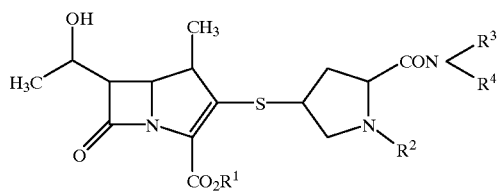

(I)

wherein $R^1$ is a group hydrolyzable in the body;

$R^2$ is selected from the group consisting of 1-alkanoyloxyalkyl, 1-alkoxycarbonyloxyalkyl and 5-methyl-2-oxo-1,3-dioxolen-4-ylmethyl;

$R^3$ and $R^4$ may be the same or different and each is a lower alkyl; or $R^3$ and $R^4$ form a cyclic amino together with the adjacent nitrogen atom selected from the group consisting of azetidinyl, pyrrolidinyl and piperidinyl, or a pharmaceutically acceptable salt thereof.

2. The carbapenem compound of claim 1, wherein $R^3$ and $R^4$ may be the same or different and each is a lower alkyl, or a pharmaceutically acceptable salt thereof.

3. A carbapenem compound of the formula (I):

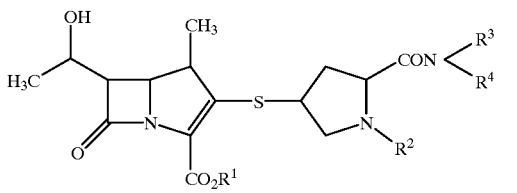

(I)

wherein $R^1$ is a group hydrolyzable in the body;

$R^2$ is 5-methyl-2-oxo-1,3-dioxolen-4-ylmethyl; and $R^3$ and $R^4$ are each methyl, or a pharmaceutically acceptable salt thereof.

4. A carbapenem compound of the formula (I):

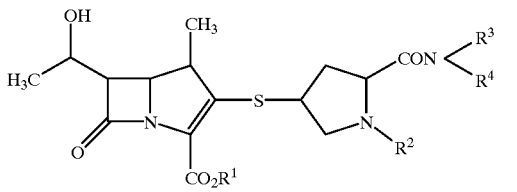

(I)

wherein $R^1$ is pivaloyloxymethyl;

$R^2$ is 5-methyl-2-oxo-1,3-dioxolen-4-ylmethyl;

$R^3$ and $R^4$ may be the same or different and each is a lower alkyl; or $R^3$ and $R^4$ form a cyclic amino together with the adjacent nitrogen atom selected from the group consisting of azetidinyl, pyrrolidinyl and piperidinyl, or a pharmaceutically acceptable salt thereof.

5. A carbapenem compound of the formula (I):

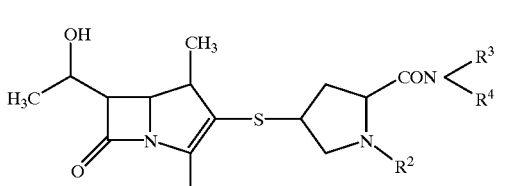

(I)

wherein $R^1$ and $R^2$ are each pivaloyloxymethyl;

$R^3$ and $R^4$ may be the same or different and each is a lower alkyl; or $R^3$ and $R^4$ form a cyclic amino together with the adjacent nitrogen atom selected from the group consisting of azetidinyl, pyrrolidinyl and piperidinyl, or a pharmaceutically acceptable salt thereof.

6. A carbapenem compound which is selected from the group consisting of pivaloyloxymethyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate, pivaloyloxymethyl (1R,5S,6S)-2-[(3S,5S)-(5-N,N-dimethylaminocarbonyl-1-pivaloyloxymethyl)

pyrrolidin-3-ylthio]-6-[(1R)-1-hydroxyethyl]-1-methylcarbapen-2-em-3-carboxylate
and pharmaceutically acceptable salts thereof.

7. A pharmaceutical composition comprising the carbapenem compound of claim 1 or a pharmaceutically acceptable salt thereof, and a pharmaceutically acceptable excipient.

8. A pharmaceutical composition comprising the carbapenem compound of claim 7 or a pharmaceutically acceptable salt thereof, and a pharmaceutically acceptable excipient.

9. A carbapenem compound of the formula (II):

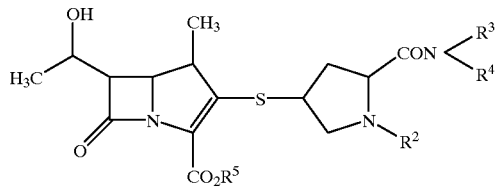

(II)

wherein
$R^2$ is selected from the group consisting of 1-alkanoyloxyalkyl, 1-alkoxycarbonyloxyalkyl and 5-methyl-2-oxo-1,3-dioxolen-4-ylmethyl;
$R^3$ and $R^4$ may be the same or different and each is a lower alkyl; or
$R^3$ and $R^4$ form a cyclic amino together with the adjacent nitrogen atom selected from the group consisting of azetidinyl, pyrrolidinyl and piperidinyl; and
$R^5$ is a hydrogen atom or a carboxyl-protecting group, or a pharmaceutically acceptable salt thereof.

10. A carbapenem compound which is selected from the group consisting of p-nitrobenzyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate,
sodium (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate
and pharmaceutically acceptable salts thereof.

11. A carbapenem compound which is selected from the group consisting of pivaloyloxymethyl (1R,5S,6S)-2-{(3S,5S)-[5-N,N-dimethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate hydrochloride, pivaloyloxymethyl (1R,5S,6S)-2-{(3S,5S)-[5-N,N-diethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate, pivaloyloxymethyl (1R,5S,6S)-2-{(3S,5S)-[5-N,N-methylethylaminocarbonyl-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate, pivaloyloxymethyl (1R,5S,6S)-2-{(3S,5S)-[5-(1-pyrrolidinylcarbonyl)-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate, pivaloyloxymethyl (1R,5S,6S)-2-{(3S,5S)-[5-(1-piperidinylcarbonyl)-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate, pivaloyloxymethyl (1R,5S,6S)-2-{(3S,5S)-[5-(1-azetidinylcarbonyl)-1-(5-methyl-2-oxo-1,3-dioxolen-4-yl)methyl]pyrrolidin-3-ylthio}-6-[(1R)-1-hydroxyethyl]-1-methylcarbapen-2-em-3-carboxylate and pharmaceutically acceptable salts thereof.

* * * * *

UNITED STATES PATENT AND TRADEMARK OFFICE
CERTIFICATE OF CORRECTION

PATENT NO.        : 6,342,494 B1                                    Page 1 of 1
APPLICATION NO. : 09/355757
DATED             : January 29, 2002
INVENTOR(S)       : Hiroshi Matsui et al.

It is certified that error appears in the above-identified patent and that said Letters Patent is hereby corrected as shown below:

① Column 19, line 7, please renumber "claim 8" as -- claim 9 --.

② Column 19, line 8, change "claim 7" to -- claim 8 --.

③ Column 19, line 10, please renumber "claim 9" as -- claim 8 --.

Signed and Sealed this

Twentieth Day of February, 2007

JON W. DUDAS
*Director of the United States Patent and Trademark Office*